United States Patent
Averina et al.

(10) Patent No.: US 10,226,634 B2
(45) Date of Patent: Mar. 12, 2019

(54) SYSTEM AND METHOD FOR ANALYZING MEDICAL DEVICE PROGRAMMING PARAMETERS

(71) Applicant: Cardiac Pacemakers, Inc., St. Paul, MN (US)

(72) Inventors: Viktoria A. Averina, Shoreview, MN (US); Pramodsingh Hirasingh Thakur, Woodbury, MN (US); Qi An, Blaine, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 15/480,195

(22) Filed: Apr. 5, 2017

(65) Prior Publication Data

US 2017/0281960 A1 Oct. 5, 2017

Related U.S. Application Data

(62) Division of application No. 14/789,500, filed on Jul. 1, 2015, now Pat. No. 9,630,014.

(60) Provisional application No. 62/020,656, filed on Jul. 3, 2014.

(51) Int. Cl.
    *A61N 1/372*     (2006.01)
    *A61N 1/365*     (2006.01)

(52) U.S. Cl.
    CPC ..... *A61N 1/37264* (2013.01); *A61N 1/36514* (2013.01); *A61N 1/36535* (2013.01); *A61N 1/36585* (2013.01); *A61N 1/37247* (2013.01)

(58) Field of Classification Search
None
See application file for complete search history.

(56) References Cited

U.S. PATENT DOCUMENTS

| | | | |
|---|---|---|---|
| 5,354,317 A * | 10/1994 | Alt | A61N 1/36542 600/595 |
| 5,948,005 A | 9/1999 | Valikai et al. | |
| 6,430,439 B1 | 8/2002 | Wentkowski et al. | |
| 6,941,167 B2 | 9/2005 | Stahmann et al. | |
| 7,406,348 B2 | 7/2008 | Stahmann et al. | |
| 8,032,208 B2 | 10/2011 | Stahmann et al. | |
| 8,150,531 B2 * | 4/2012 | Skelton | A61B 5/103 607/62 |

(Continued)

OTHER PUBLICATIONS

File History for Related U.S. Appl. No. 14/789,500 downloaded May 22, 2017 (167 pages).

(Continued)

*Primary Examiner* — Brian T Gedeon
(74) *Attorney, Agent, or Firm* — Pauly, DeVries Smith & Deffner LLC

(57) ABSTRACT

The technology disclosed herein relates to a system and method for analyzing medical device programming parameters. One aspect of the current technology is a method where an overall performance metric is detected for a cardiac medical device that is outside of a threshold at a first cardiac location in a patient. Processing circuitry identifies a first operating condition and sensing circuitry measures a first sensor response during the first operating condition. An adjustment is proposed to one or more programming parameters of the medical device based on the performance metric, the first operating condition, and the sensor response to the operating condition.

7 Claims, 10 Drawing Sheets

(56) References Cited

U.S. PATENT DOCUMENTS

| | | |
|---|---|---|
| 8,364,263 B2 | 1/2013 | Siejko et al. |
| 8,380,309 B2 | 2/2013 | Bruns et al. |
| 8,744,579 B2 | 6/2014 | Parikh et al. |
| 9,320,906 B2 | 4/2016 | Maskara et al. |
| 9,630,014 B2 | 4/2017 | Averina et al. |
| 2008/0294217 A1* | 11/2008 | Lian .................... A61N 1/3712 607/28 |
| 2011/0034812 A1 | 2/2011 | Patangay et al. |
| 2012/0310101 A1 | 12/2012 | Patangay et al. |
| 2016/0001088 A1 | 1/2016 | Averina et al. |

OTHER PUBLICATIONS

Lewis, R. P. et al., "A Critical Review of the Systolic Time Intervals," Circulation 1977 vol. 56, No. 2 Aug. 1977, pp. 146-158.
Madras, et al., "Posture-Dependent AV block as a complication of robotic cardiac surgery: ECG and cardiac MRI findings," EP Europace 2013 vol. 13, issue suppl 1, i38-39.
Weissler, Arnold M. et al., "Systolic Time Intervals in Heart Failure in Man," Circulation 1968 vol. 37, No. 2 Feb. 1968, 149-159.
Whellan, David J. et al., "Combined Heart Failure Device Diagnostics Identify Patients at Higher Risk of Subsequent Heart Failure Hospitalizations," Journal of the American College of Cardiology 2010 vol. 55, No. 17 Apr. 27, 2010, pp. 1803-1810.

* cited by examiner

SYSTEM AND METHOD FOR ANALYZING MEDICAL DEVICE PROGRAMMING PARAMETERS

This application is a divisional of U.S. Non-Provisional application Ser. No. 14/789,500, filed Jul. 1, 2015, which claims the benefit of U.S. Provisional Application No. 62/020,656 filed Jul. 3, 2014, the content of which is herein incorporated by reference in its entirety.

TECHNOLOGICAL FIELD

The technology disclosed herein generally relates to medical device programming parameters. More particularly, the technology disclosed herein relates to a system and method for analyzing medical device programming parameters.

BACKGROUND

System performance metrics can be valuable to track for therapies administered by implantable cardiac rhythm management devices. The pacing prevalence, for example, can be a strong indicator of whether the therapy being administered is appropriate for the patient. Very little guidance has typically been provided to medical practitioners to aid them in identifying potential issues from the performance metrics and/or recommending parameter changes that are likely to remedy the issue.

SUMMARY

The technology disclosed herein relates to a system and method for analyzing medical device programming parameters. One aspect of the current technology is a method where an overall performance metric is detected for a cardiac medical device that is outside of a threshold at a first cardiac location in a patient. Processing circuitry identifies a first operating condition and sensing circuitry measures a first sensor response during the first operating condition. An adjustment is proposed to one or more programming parameters of the medical device based on the performance metric, the first operating condition, and the sensor response to the operating condition. In addition or alternatively, one or more programming parameters of the cardiac medical device are automatically changed based on the proposed adjustment.

In one aspect of the technology, the cardiac medical device overall performance metric is pacing prevalence. In another aspect of the technology, the first operating condition is one of the group consisting of: patient posture, metabolic state, exertion level, patient sleep status, heart rate and time-of-day. In another aspect, the overall performance metric and the proposed adjustment are displayed on a user interface. In addition or alternatively, a conclusion regarding patient condition is displayed on a user interface, where the conclusion is based on the overall performance metric, the first operating condition, and the first sensor response to the first operating condition. In one aspect of the technology, the first sensor response to the first operation condition comprises one in the group consisting of: the overall performance metric, heart sound amplitudes, cardiac timing intervals, respiratory measure, and heart rate.

In addition or alternatively, one aspect of the technology is measuring a second sensor response during a second operating condition. In such an aspect, the first sensor response and the second sensor response are each measured from the same sensor modality, and the adjustment is proposed based on comparing the first sensor response to the second sensor response. In addition or alternatively, a second sensor response is measured during the first operating condition, where the first sensor response is measured from a different sensor modality than the second sensor response. The adjustment is proposed based on comparing the second sensor response and the first sensor response.

In addition or alternatively, the proposed adjustment is a recommendation of a shortened intraventricular delay upon determining left ventricular pacing is below the threshold and right ventricular pacing is not below the threshold. In addition or alternatively, the conclusion is loss of capture and the proposed adjustment to programming parameters is increasing medical device pacing voltage.

In one aspect of the technology, the system identified loss of capture by switching the cardiac medical device pacing status operating condition to OFF and operating the cardiac medical device with pacing OFF. The sensed S1 amplitude is recorded, and the cardiac medical device pacing status is switched to ON. The cardiac medical device is operated with pacing ON and the paced S1 amplitude is recorded. The paced amplitude is compared to the sensed amplitude, wherein the sensed amplitude is larger than or substantially equal to the paced amplitude.

In addition or alternatively, a system is disclosed having circuitry configured to determine an overall performance metric for the cardiac medical device that is outside of a threshold at a first cardiac location in a patient. Sensing circuitry is configured to measure a first sensor response during a first operating condition and processing circuitry is configured to propose an adjustment to one or more programming parameters of the medical device based on the performance metric, the first operating condition, and the sensor response to the operating condition. In one aspect of the technology, the first operating condition is one of the group consisting of: patient posture, metabolic state, exertion level, patient sleep status, heart rate and time-of-day. In another aspect of the technology, the cardiac medical device overall performance metric is pacing prevalence.

In addition or alternatively, a system is disclosed having a cardiac medical device configured to be implanted in a patient, where the medical device has sensing circuitry configured to sense sufficient data to determine a first overall performance metric at a first cardiac location of a patient. Processing circuitry is in communication with the sensing circuitry and is configured to identify a first performance metric during a first operating condition and a second performance metric during a second operating condition. A user interface is configured to display an association of the first performance metric with the first operating condition and the second performance metric to the second operating condition.

In addition or alternatively, a system disclosed herein has an accelerometer configured to determine patient posture. The accelerometer is in communication with the processing circuitry, where the first operating condition is recumbent patient posture and the second operating condition is upright patient posture. In addition or alternatively, the first operating condition is nighttime and the second operating condition is day time. In one aspect of the system, the performance metric is pacing prevalence.

In addition or alternatively, the system disclosed herein has a user interface, wherein the system is configured to display a programming recommendation on the user interface based on the first performance metric, the second performance metric, the first operating condition, and the second operating condition. In one aspect of the technology, the programming recommendation is to evaluate loss of capture.

In addition or alternatively, the sensing circuitry of the system is further configured to determine a second overall performance metric at a second cardiac location of a patient. The processing circuitry is further configured to associate a third performance metric with the first operating condition and a fourth performance metric with the second operating condition. Other aspects of the technology are disclosed.

BRIEF DESCRIPTION OF THE DRAWINGS

The current technology may be more completely understood and appreciated in consideration of the following detailed description of various embodiments in connection with the accompanying drawings.

DETAILED DESCRIPTION

Figure 1:
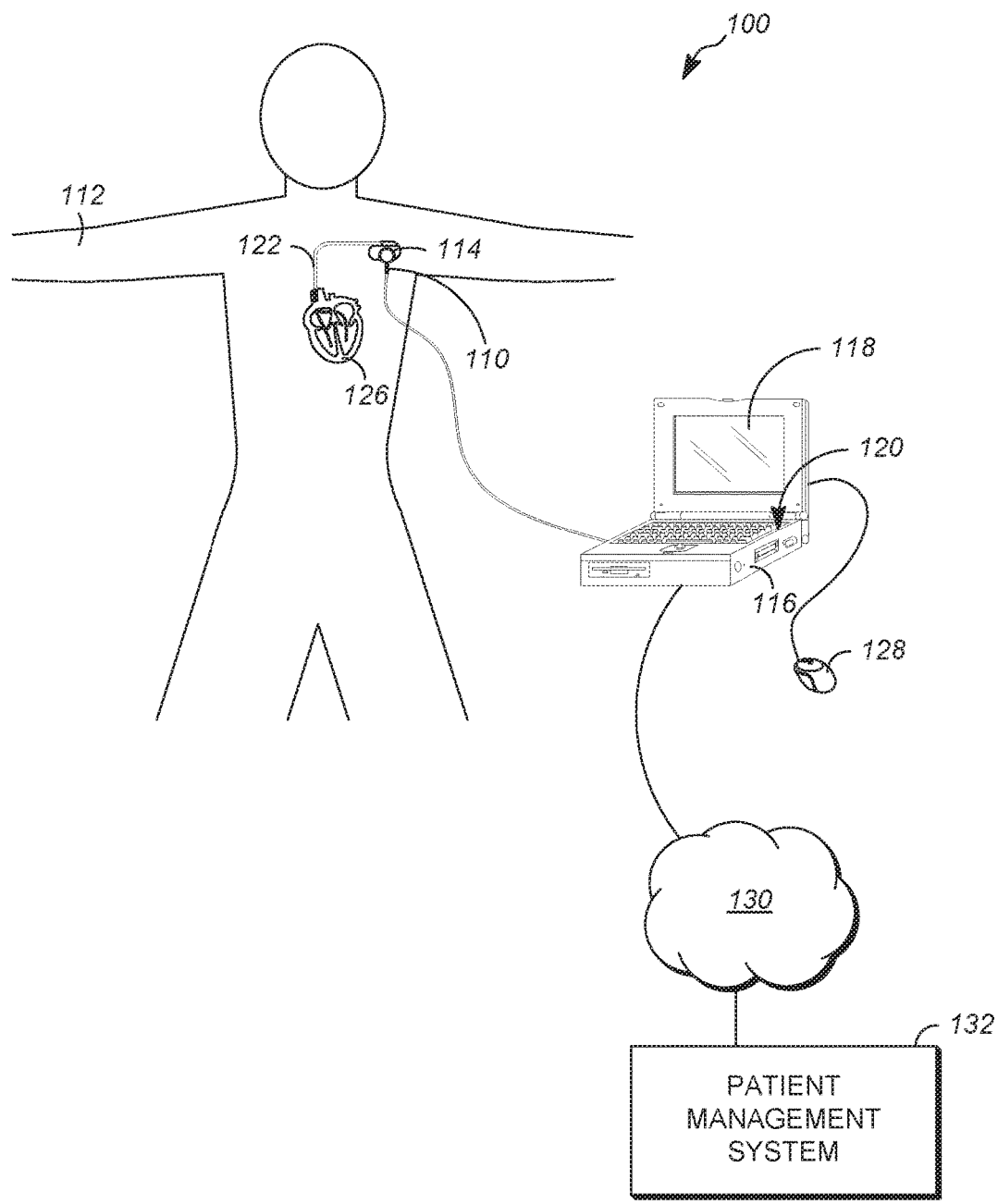
FIG. 1 is a schematic diagram of an exemplary implementation of a cardiac rhythm management (CRM) system, including an implanted CRM device, a programming device, and a patient management computer system, consistent with at least one embodiment of the technology disclosed herein.

The technology disclosed herein relates to a system and method for analyzing medical device programming parameters. One aspect of the current technology is a method where an overall performance metric is detected for a cardiac medical device that is outside of a threshold at a first cardiac location in a patient. Processing circuitry identifies a first operating condition and sensing circuitry measures a first sensor response during the first operating condition. An adjustment is proposed to one or more programming parameters of the medical device based on the performance metric, the first operating condition, and the sensor response to the operating condition. In addition or alternatively, one or more programming parameters of the cardiac medical device are automatically changed based on the proposed adjustment.

In one aspect of the technology, the cardiac medical device overall performance metric is pacing prevalence. In another aspect of the technology, the first operating condition is one of the group consisting of: patient posture, metabolic state, exertion level, patient sleep status, heart rate and time-of-day. In another aspect, the overall performance metric and the proposed adjustment are displayed on a user interface. In addition or alternatively, a conclusion regarding patient condition is displayed on a user interface, where the conclusion is based on the overall performance metric, the first operating condition, and the first sensor response to the first operating condition. In one aspect of the technology, the first sensor response to the first operation condition comprises one in the group consisting of: the overall performance metric, heart sound amplitudes, cardiac timing intervals, respiratory measure, and heart rate.

In addition or alternatively, one aspect of the technology is measuring a second sensor response during a second operating condition. In such an aspect, the first sensor response and the second sensor response are each measured from the same sensor modality, and the adjustment is proposed based on comparing the first sensor response to the second sensor response. In addition or alternatively, a second sensor response is measured during the first operating condition, where the first sensor response is measured from a different sensor modality than the second sensor response. The adjustment is proposed based on comparing the second sensor response and the first sensor response.

In addition or alternatively, the proposed adjustment is a recommendation of a shortened intraventricular delay upon determining left ventricular pacing is below the threshold and right ventricular pacing is not below the threshold. In addition or alternatively, the conclusion is loss of capture and the proposed adjustment to programming parameters is increasing medical device pacing voltage.

In one aspect of the technology, the system identified loss of capture by switching the cardiac medical device pacing status operating condition to OFF and operating the cardiac medical device with pacing OFF. The sensed S1 amplitude is recorded, and the cardiac medical device pacing status is switched to ON. The cardiac medical device is operated with pacing ON and the paced S1 amplitude is recorded. The paced amplitude is compared to the sensed amplitude, wherein the sensed amplitude is larger than or substantially equal to the paced amplitude.

In addition or alternatively, a system is disclosed having circuitry configured to determine an overall performance metric for the cardiac medical device that is outside of a threshold at a first cardiac location in a patient. Sensing circuitry is configured to measure a first sensor response during a first operating condition and processing circuitry is configured to propose an adjustment to one or more programming parameters of the medical device based on the performance metric, the first operating condition, and the sensor response to the operating condition. In one aspect of the technology, the first operating condition is one of the group consisting of: patient posture, metabolic state, exertion level, patient sleep status, heart rate and time-of-day. In another aspect of the technology, the cardiac medical device overall performance metric is pacing prevalence.

In addition or alternatively, a system is disclosed having a cardiac medical device configured to be implanted in a patient, where the medical device has sensing circuitry configured to sense sufficient data to determine a first overall performance metric at a first cardiac location of a patient. Processing circuitry is in communication with the sensing circuitry and is configured to identify a first performance metric during a first operating condition and a second performance metric during a second operating condition. A user interface is configured to display an association of the first performance metric with the first operating condition and the second performance metric to the second operating condition.

In addition or alternatively, a system disclosed herein has an accelerometer configured to determine patient posture. The accelerometer is in communication with the processing circuitry, where the first operating condition is recumbent patient posture and the second operating condition is upright patient posture. In addition or alternatively, the first operating condition is nighttime and the second operating condition is day time. In one aspect of the system, the performance metric is pacing prevalence.

In addition or alternatively, the system disclosed herein has a user interface, wherein the system is configured to display a programming recommendation on the user interface based on the first performance metric, the second performance metric, the first operating condition, and the second operating condition. In one aspect of the technology, the programming recommendation is to evaluate loss of capture.

In addition or alternatively, the sensing circuitry of the system is further configured to determine a second overall performance metric at a second cardiac location of a patient. The processing circuitry is further configured to associate a third performance metric with the first operating condition and a fourth performance metric with the second operating condition. Other aspects of the technology are disclosed.

FIG. 1 is a schematic of an exemplary cardiac rhythm management (CRM) system 100, consistent with at least one embodiment of the technology disclosed herein. The system 100 can include an implantable medical device 114 implanted within a patient 112 that can be in communication with a programming device 116 or other user interface. The programming device 116 is generally in communication with a patient management system 132 through a communication link 130.

Medical Device

The implantable medical device 114 can include pacing circuitry that is configured to execute pacing functionality. The implantable medical device 114 can be of various types such as, for example, a pacemaker, a cardioverter-defibrillator, a cardiac resynchronization device, or the like. The implantable medical device 114 can include one or more leads 122 disposed in or near the patient's heart 126. In some embodiments, the implantable medical device does not include leads. In one embodiment, the implantable medical device does not include leads and is configured to be implanted just below the patient's skin and provide electrical impulses to stimulate the heart.

The implantable medical device 114 can include one or more implantable sensors having the relevant sensing circuitry to gather appropriate data. The data that is gathered can be medical device 114 data including performance metrics, patient 112 physiological data, and data reflecting various operating conditions of the system, where the term "operating condition" is generally defined herein as a particular aspect of the operating environment of the medical device 114 that is outside of the direct control of the medical device 114.

Example medical device 114 data can be collected such as paced heartbeats, lead impedance, and pacing prevalence such as pacing percentage or sensed percentage. There are a variety of different types of pacing/sensed percentage measurements that can be used such as prevalence of ventricular paced response to atrial paced beats, prevalence of ventricular sensed response to atrial paced beats, prevalence of ventricular paced response to atrial sensed beats, and so on.

Example patient 112 physiological data that can be collected includes patient cardiac activity including sensed heartbeats, heart rate, cardiac events, loss of capture, blood pressure, and respiration rate, as examples. Example data associated with medical device operating conditions can be patient posture, such as recumbent posture versus upright posture, patient exertion level, such as inactive, active, sedentary, light, moderate or vigorous, patient sleep status, such as awake or asleep, and time-of-day, such as day time or nighttime. Other types of data can also be collected by the medical device 114. In some embodiments, the data that is collected by the medical device 114 can be an indicator of a particular operating condition, rather than directly representing the particular operating condition. For example, heart rate can be collected by the medical device as an indicator of patient exertion level, patient sleep status or time-of-day. In another example, time-of-day data, patient posture data, or patient metabolic state data can be collected as an indicator of patient sleep state.

The implantable medical device 114 can include a variety of sensors that are configured to sense the medical device data, patient physiological data, and operating condition data such as, for example, an accelerometer, pacing electrodes, blood pressure sensors, respiration sensors and/or other sensors. Each of the sensors can be configured for implantation in the patient 112, although in some embodiments, one or more sensors can be external to the patient 112. In at least one embodiment, one or more external sensors can be used in conjunction with implanted sensors to gather patient data. Those having skill in the art will appreciate the particular processing circuitry configurations for collecting relevant data, some of which will be described with reference to FIG. 13.

With regard to medical device sensing circuitry for sensing operating conditions such as patient posture or time-of-day, an accelerometer or clock can be incorporated in the medical device 114. The accelerometer or clock can be configured for implantation in the patient 112 in at least one embodiment. In another embodiment, sensing circuitry for sensing operating conditions can be external to the patient 112 and separate from the medical device 114. For example, in some embodiments the operating conditions can be selected by the patient 112 or a caregiver through a user interface. In one particular example, the patient 112 can indicate that they are awake or asleep through a user interface that is in communication with processing circuitry of the system 100. In another example, the patient 112 can indicate that they are in an upright or recumbent posture through a user interface that is in communication with processing circuitry of the system 100. Other approaches can also be used to determine patient posture.

Programming Device Details

In addition to being in selective communication with the implantable medical device 114, the programming device 116 can also be in communication with the implantable sensors of the implantable medical device 114, and/or one or more other implantable sensors. In some embodiments, communication between the implantable medical device 114 and the programming device 116 can be via inductive communication through a wand 110 held on the outside of the patient 112 near the implantable medical device 114. However, in other embodiments, communication can be carried out via radiofrequency transmission, acoustically, or the like. The implantable medical device 114 can be configured to store data over a period of time and periodically communicate with the programming device 116 in order to transmit some or all of the stored data.

The programming device 116 can be for example, a programmer, a programmer/recorder/monitor device, a computer, an advanced patient management system, a personal digital assistant (PDA), or the like. The programming device 116 is one example of a user interface. As used herein, the term programming device 116 refers to a device that programs implanted devices and records data from implanted devices. The programming device 116 may also allow monitoring of the medical device 114. Exemplary programmer/recorder/monitor devices include the Model 3120 Programmer, available from Boston Scientific Corporation, Natick, Mass. The programming device 116 can include a user interface such as a keyboard 120, a mouse 128, a touch screen, or more than one such device to receive user input. The programming device 116 can also include a video output channel and a user interface such as a video display 118 for displaying videos, user prompts, device operation parameters, settings, recommendations, and the like. In addition, the video display 118 can also be equipped with a touch screen, making it into a user input device as well.

The programming device 116 can display real-time data and/or stored data graphically, such as in charts or graphs, and textually through the user interface screen. The programming device 116 can display parameters associated with the medical device 114. Parameters associated with the medical device 114 can be device operational parameters, patient indications relevant to the medical device 114, and the like. In at least one embodiment, the parameters associated with the medical device 114 can include system-recommended parameters or proposed parameter adjustments that are formulated by the system. In addition, the programming device 116 can prompt a user for particular data. In addition, the programming device 116 can also notify a clinical user of an identified patient condition or operating conditions impacting system performance. The notification can be in the form of an alert on the programming device screen 118, a sound, a text display, or a combination of these. The programming device 116 can also display options for a therapy appropriate for the identified patient condition and/or operating conditions. The programming device 116 can display one or more selectable options for a therapy appropriate for the identified patient/operating condition and can receive input from the clinical user selecting one of the options.

The programming device 116 can also display a rationale for the conclusion that a patient condition or operating condition has been identified. Also, in response to an input to turn off or inappropriately modify the therapy appropriate for the condition, the programming device 116 can deliver an alert to a user communicating that the requested modification is inappropriate for the identified condition.

The programming device 116 can input and store a user's response to the various programming prompts. The programming device 116 can also display indications of system confidence levels relative to particular data or operation parameters based on a variety of factors including sensor reliability, age of a patient's electronic files, past accuracy of the data or operation parameters, and the like. The programming device can also display guidance to a user regarding data accuracy.

In various embodiments, the programming device 116 is in communication with the patient management system 132. The patient management system 132 can additionally be in communication with electronic patient medical records in a variety of embodiments. The communication link 130 between the programming device 116 and the patient management system 132 may be via phone lines, the Internet, or any other data connection. In another embodiment, the programming device 116 is not in direct communication with a patient management system 132, but can be in indirect communication with the patient management system 132. In another embodiment, the programming device is not in communication with a patient management system 132.

The programming device 116 is capable of changing the operational parameters of the medical device 114, and is therefore referred to as a programmer. Typically, programmers are used to interface with medical devices in a clinic or hospital setting. In this context, the user of the programming device 116 is a clinician, physician or trained technician.

Remote Programming Embodiment

Figure 2:
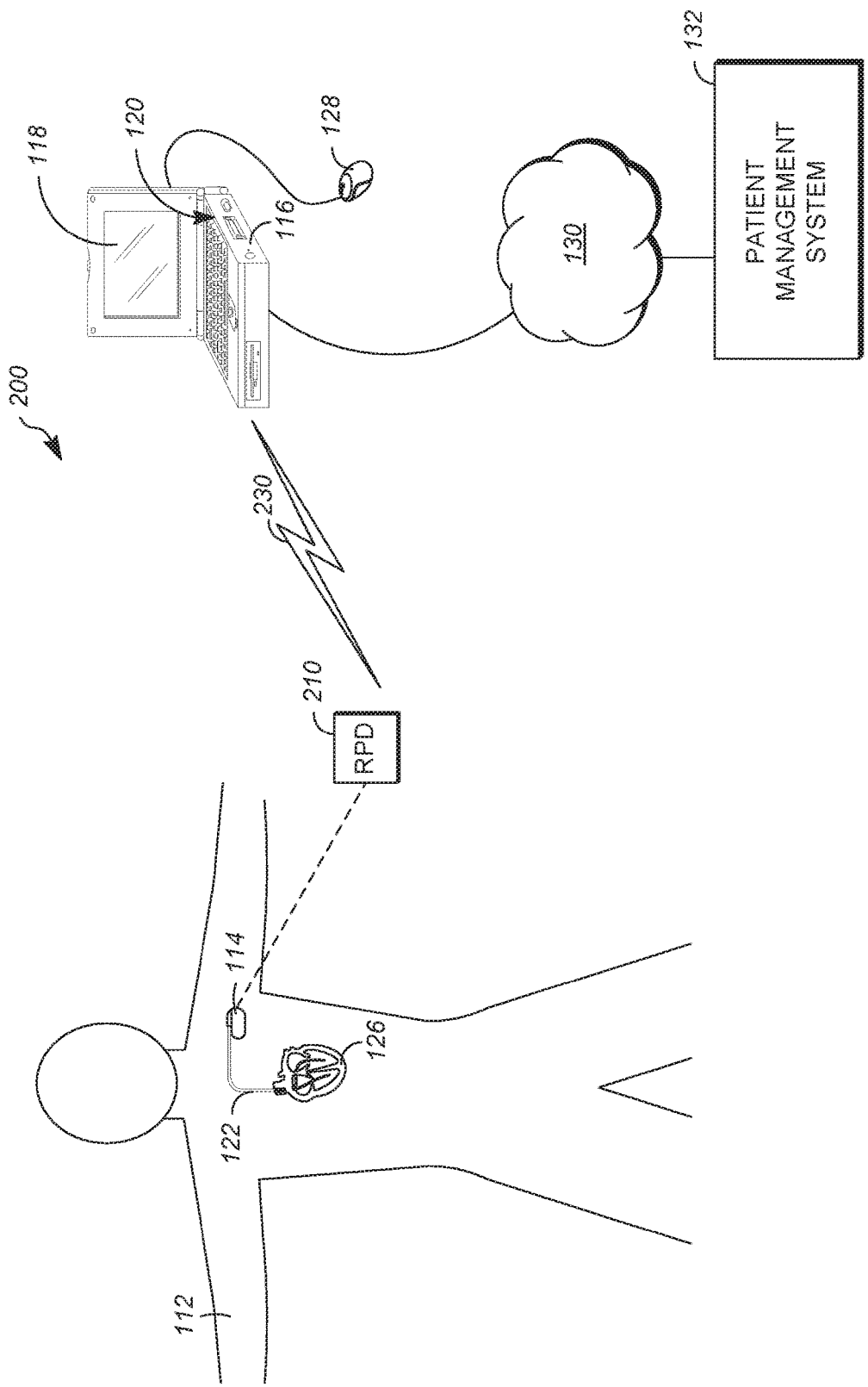
FIG. 2 is a schematic diagram of another exemplary implementation of a CRM system, including an implanted CRM device, a remote programming device, a programming device, and a patient management computer system, consistent with at least one embodiment of the technology disclosed herein.

Now referring to FIG. 2, a CRM system 200 is illustrated which is designed for use when the programming device 116 and the patient 112 are in different locations, so that the programming device 116 is remote from the patient 112 and not physically present in the same space as the patient 112. For example, the patient 112 may be at his or her home while the clinician and the remote programming device 116 is at a hospital which is a few miles away or hundreds of miles away Like reference numbers between FIG. 1 and FIG. 2 indicate like elements. In the CRM system 200 of FIG. 2, a remote programming device 210 is in the patient 112 location and establishes communication with the implantable medical device 114. Communication between the remote programming device 210 and the implantable medical device 114 can be carried out by radiofrequency transmission, acoustically, or by inductive communication using a wand held on the outside of the patient 112 near the device 114.

The remote programming device 210 is in communication with a local programming device 116. The communication link 230 between the local programming device 116 and the remote programming device 210 may be via phone lines, the Internet, or any other data connection. Other details of the programming device 116 and the implantable medical device 114 are similar to as described with respect to FIG. 1.

System Processes

Referring to embodiments consistent with both FIGS. 1 and 2, while the sensing circuitry typically can be associated with the implantable medical device 114, processing circuitry associated with the system 100 can be distributed across the medical device 114, the programmer 116, the patient management system 132, and other devices that can be incorporated in the system. The processing circuitry could be entirely within the implantable medical device, in some examples. Generally the sensing circuitry of the medical device 114 is configured to sense sufficient data to determine medical device performance metrics and patient physiological data although, as described above, the sensing circuitry can also be used to determine various operating conditions as well.

In at least one embodiment, the system 100/200 is configured to detect a performance metric that is the overall pacing prevalence of a system at a particular cardiac location of the patient 112, where the overall pacing prevalence is generally an expression of the overall number of paced beats compared to the overall number of sensed beats. Pacing prevalence can be specifically expressed in a variety of ways, including as a paced percentage or a sensed percentage, but those having skill in the art will appreciate that any expression of pacing prevalence will be sufficient to practice the technology disclosed herein.

The system 100/200 is generally configured to collect data during various operating conditions. Particularly, sensing circuitry is configured to measure sensor responses during each operating condition. Processing circuitry of the system 100 is generally configured to identify operating conditions and recognize data sensed during one operating condition and data sensed during another operating condition. Such a configuration has the advantage of identifying a potential relationship between the operating condition and changes in sensor response. For example, processing circuitry of the system can be configured to associate a first pacing prevalence as within a first operating condition and a second pacing prevalence as within a second operating condition. The first operating condition and the second operating condition can be mutually exclusive in at least one embodiment. For example, the first operating condition can be recumbent patient posture, and the second operating condition can be upright patient posture. In another example, the first operating condition can be nighttime, and the second operating condition can be day time.

The processing circuitry of the system is generally configured to propose a programming parameter adjustment based on a sensed performance metric, an operating condition, and the measured sensor response during the operating condition. So, as in the embodiment described above, the programming recommendation can be based on the first pacing prevalence, the second pacing prevalence, the first operating condition and the second operating condition. The proposed adjustment can be displayed on a user interface such as the video display 118 of the programming device 116 of FIGS. 1 and 2. The proposed adjustment can also be communicated in other ways such as by audio communication or a print-out. In a variety of embodiments the user interface of the system 100, such as the video display 118, is configured to display an overall performance metric of the medical device and the proposed adjustment. In some of those embodiments the user interface is further configured to display an operating condition and the sensor response during that operating condition, where the technical effect is that a clinician can consider the operating conditions view how sensor responses are impacted by the operating conditions. In at least one embodiment, the user interface is configured to display the overall performance metric, the operating condition, the sensor response during the operating condition, and the proposed adjustment simultaneously on a single screen.

Now more particular system operations will be described with regard to the flow charts depicted in FIGS. 3-6.

Figure 3:
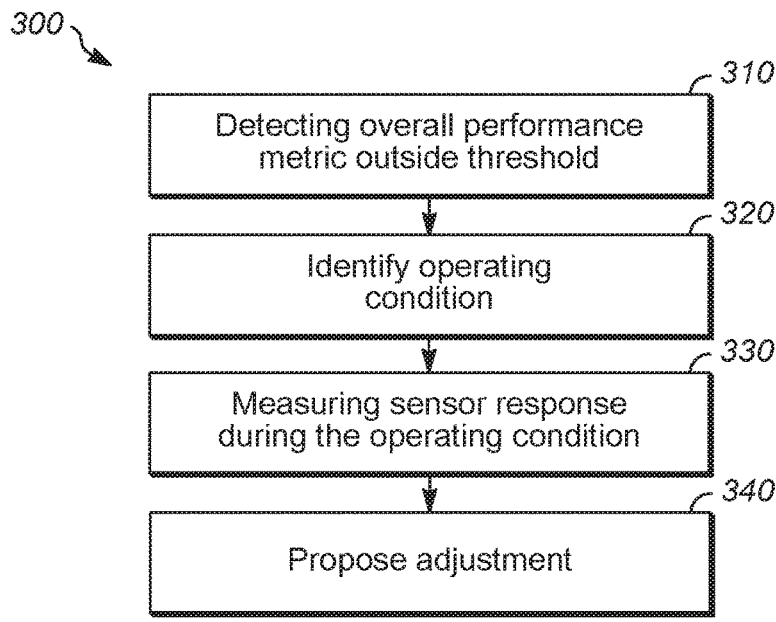
FIG. 3 is a flow chart depicting one method consistent with the technology disclosed herein.

FIG. 3 depicts a flow chart associated with an example method 300 consistent with the technology disclosed herein. Generally, a performance metric being outside of a threshold is detected 310, an operating condition is identified 320, sensor response during the operating condition is measured 330, and an adjustment is proposed 340. In a variety of embodiments each of the elements of the method 300 can be executed by processing circuitry distributed across the medical device 114, the programming device 116, the patient management system 132, and other components, as will be appreciated by those having skill in the art.

Generally the overall performance metric is associated with a cardiac medical device. In some instances the overall performance metric can be associated with the cardiac medical device at a particular cardiac location in a patient. In at least one embodiment the overall performance metric of the cardiac medical device that is detected by the system is the pacing prevalence at a particular cardiac location in the patient. Pacing prevalence is generally an expression of the relationship between the number of beats paced by the medical device ("paced beats") and the number of sensed beats initiated by the patient's body without a pace from the cardiac medical device ("sensed beats") at a particular cardiac location. In at least one embodiment, the pacing prevalence can be a percentage of the paced beats relative to the total beats, and in another embodiment, the pacing prevalence can be a percentage of the sensed beats relative to the total beats. Other ways of expressing the relationship between paced beats and sensed beats can also be used.

Detecting whether the performance metric is outside of a threshold 310 is dependent on many factors, as will be appreciated. The threshold that is used by the system will largely depend on the type of performance metric that is considered, the type of components within the system, the patient condition, and others. In some implementations the threshold will be a maximum threshold, and in other implementation the threshold will be a minimum threshold. In yet other implementations multiple thresholds can be used.

Detecting whether the pacing prevalence is outside of a threshold 310 is generally at a first cardiac location of the patient and is dependent on the type of cardiac pacing being implemented through the medical device. The pacing prevalence being outside of the threshold 310 generally correlates to the programming parameters of the medical device being inappropriate for proper treatment of the patient. When a patient needs cardiac resynchronization therapy, higher pacing percentages generally lead to better outcomes. In situations where the medical device is providing cardiac resynchronization therapy to the patient, for example, the threshold is a minimum threshold limit.

For many patients who are not chronotopically incompetent and do not need pacing but do need the safeguard of a defibrillator, a lower pacing percentage generally lead to better outcomes. In situations where the medical device is an implantable cardioverter-defibrillator (ICD), the threshold will generally be a maximum threshold limit. In one particular embodiment, the implanted medical device is a cardiac rhythm therapy device and the detecting whether a performance metric is outside of a threshold 310 is detecting whether the pacing prevalence is above a threshold The operating condition that is identified 320 generally can be an operating condition that is suspected to impact medical device performance. The operating condition can be one of the group consisting of: upright patient posture, recumbent patient posture, metabolic state, exertion level, day time, and nighttime. Other operating conditions can certainly be identified by the system. As described above with reference to FIGS. 1 and 2, the system can have sensing circuitry that is configured to sense various operating conditions. For example, patient posture can be determined with an accelerometer.

Measuring sensor response during the operating condition 330 generally entails that the sensing circuitry of the system collects data during the particular operating condition. In a variety of embodiments, the processing circuitry of the system identifies and associates the collected sensor response data with the particular operating condition. The particular type of sensor response considered by the system can depend of a variety of factors that are dependent on the particular implementation of the system, but will generally be sensor data that is relevant to considering whether medical device parameter settings are appropriate for the patient based on the performance metric and the operating condition.

Measured sensor responses can be, as examples, heart sound amplitudes, cardiac timing intervals, respiratory measures, and heart rate. Example cardiac timing intervals can include a pre-ejection period, ejection timing, systolic time intervals and diastolic intervals. Cardiac timing intervals can be measured using one of or combinations of heart sounds signals, intracardiac (See, for example, U.S. Pat. No. 8,364,263) or carotid impedance signals, carotid or pulmonary artery pulse pressure signals (See, for example, U.S. Pub. No. 2011/0034812), and/or electrogram signals. Pre-ejection period is generally defined as the interval between the initiation of electrical systole and start of ejection. Q-point on the electrogram is the true marker of initiation of electrical systole, either Q-point and/or R-marker from the device can be used as a reference for initiation of electrical systole. Q-point can be obtained from an external surface EKG or from a global electrogram signal from an implanted device such as the shock channel electrogram (See, for example, U.S. Pub. No. 2012/0310101). Start of ejection can be estimated using timing of a reference feature on the first heart sound (S1) or some feature out of intracardiac impedance just as timing of the peak derivative. Ejection time is measured from the start of ejection to the end of ejection. S2 heart sounds can be used as a marker for end of ejection. Total systolic time interval is measured from the initiation of electrical systole to end of ejection. Diastolic interval can be measured by subtracting total systolic time interval from RR interval.

In one particular example, the measured sensor response during an operating condition can be a particular cardiac performance metric during that operating condition. This is contrasted with the overall performance metric of the medical device, which is generally the performance metric associated with the medical device during all operating conditions.

Proposing an adjustment 340 generally involves proposing an adjustment to one or more programming parameters of the medical device. The proposed adjustment 340 can be based on the pacing prevalence being outside the threshold 310 and the measured sensor response during the operating condition 330, for example, although other factors can also be taken into consideration. The proposed adjustment to programming parameters can include a variety of parameters such as lower rate limit, right ventricular pacing threshold, left ventricular pacing threshold, dynamic atrioventricular delay response factor, paced atrioventricular delay, interventricular delay, and ventricular rate regulation. Atrioventricular (A/V) delay can be RA-RV delay, RA-LV delay, and LA-LV delay, as examples. In at least one embodiment the system can be configured to automatically change one or more programming parameters of the cardiac medical device based on the proposed adjustment.

The method disclosed herein can further include displaying relevant information to the user such as the performance metric, the sensor response during the operating condition 330, and the proposed adjustment 340. Such data can be displayed on a user interface. Such data can be displayed on a single screen on the user interface in at least one embodiment. Such data can be displayed simultaneously on a single screen on the user interface in at least one embodiment. In some embodiments, the system is also configured to display a conclusion regarding the patient condition based on the overall performance metric and the sensor response during the operating condition. A conclusion could take the form of a summary, a recommendation or both. Such a system configuration has the technical effect of drawing a user's attention to a potential relationship between inappropriate medical device settings during specific operating conditions.

Figure 4:
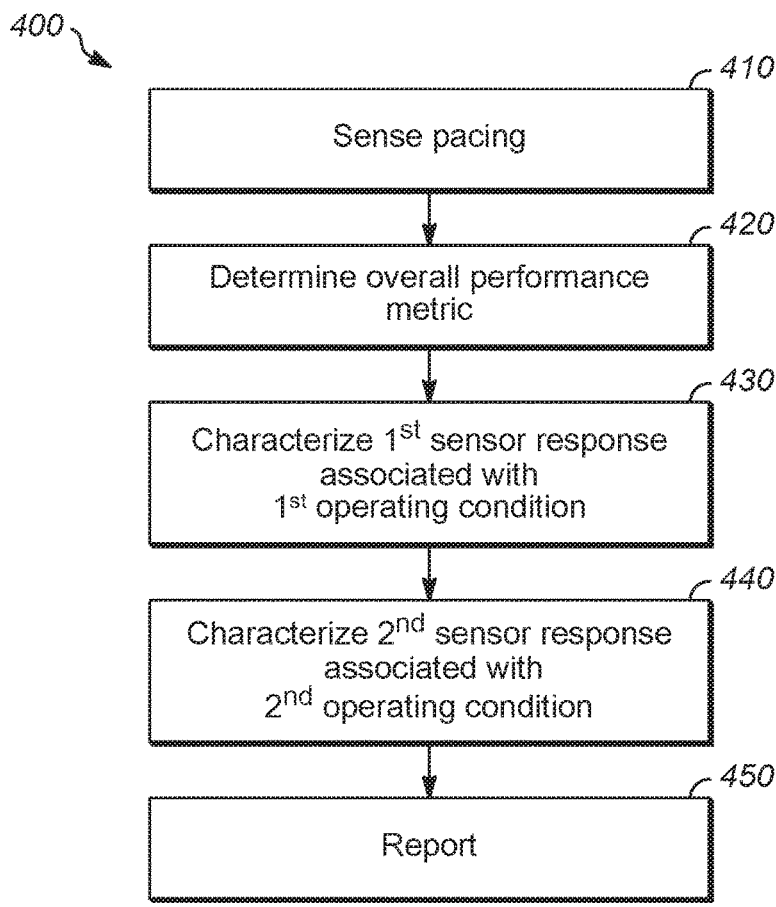
FIG. 4 is another flow chart depicting another method consistent with the technology disclosed herein.

FIG. 4 depicts another method consistent with the technology disclosed herein. Pacing is sensed 410, an overall performance metric is determined 420, a first sensor response is characterized that is associated with a first operating condition 430, a second sensor response is characterized that is associated with a second operating condition 440, and data is reported 450.

The pacing is sensed 410 consistently with the medical device sensing circuitry described above with reference to FIG. 1 and will generally include sensing paced and sensed heartbeats in addition to other data, if appropriate. Based on at least the pacing data, an overall medical device overall performance metric can be determined. The overall performance metric can be determined by processing circuitry of the system, for example. Although not depicted in FIG. 4, in some embodiments, determining the overall performance metric also includes determining whether the overall performance metric is outside of a threshold, such as described in relation to FIG. 3, above.

Systems consistent with the current embodiment are generally configured to recognize at least a first operating condition and a second operating condition, and characterize a first sensor response that is associated with the first operating condition 430 and a second sensor response that is associated with the second operating condition 440. As described above, medical devices consistent with the technology disclosed herein are generally configured to measure sensor response during the various operating conditions such that the first sensor response is measured during the first operating condition and the second sensor response is measured during the second operating condition. The sensor responses that are measured by the medical device are characterized by system processing circuitry to describe the sensor response during each operating condition.

As mentioned above, in some embodiments the sensor response can be a performance metric of the medical device, where the overall performance metric characterizes the medical device during all operating conditions and a particular performance metric characterizes the medical device during a particular operating condition. For example, where the operating conditions are day time and nighttime, the system can be configured to characterize a day time performance metric and a nighttime performance metric, and determine an overall performance metric that characterizes the medical device performance over an entire day. In another example, where the operating conditions are the patient being recumbent posture and the patient being in upright posture, the system can be configured to characterize a recumbent performance metric and an upright performance metric, in addition to determining an overall performance metric that characterizes the medical device performance regardless of patient posture.

A report is generated 450 based at least on the determination of the overall performance metric 420, the first sensor response during the first operating condition 430, and the second sensor response during the second operating condition 440. The report 450 can be displayed on a user interface and, in one embodiment, the report display includes the overall performance metric, the first sensor response, and the second sensor response on a single screen of the user interface. In a variety of embodiments, generating a report 450 is achieved by analyzing the overall performance metric, the first sensor response and the second sensor response. In a variety of embodiments, the processing circuitry compares the first sensor response to the second sensor response. Generally, the first sensor response and the second sensor response are measured from the same sensor modality, allowing the system to determine how an operating condition changes the sensor response. As used herein, the phrase "same sensor modality" means a reading from the same sensor or from different sensors but of the same measured physiological characteristic, such as heart rate or paced beats, though there may be a difference in an operating condition at the time the two measurements are taken. As used herein, the phrase "different sensor modality" means a reading from different sensors or of different physiological characteristics. For example, if the first sensor response is the S1 amplitude at night, and the second sensor response is the S1 amplitude during the day time, then the first sensor response and the second sensor response are measured from the same sensor modality and a comparison of the two reflects how day time and nighttime impacts S1 amplitude.

In one alternative embodiment that is not depicted, however, the first sensor response and the second sensor response can be measured from different sensor modalities and can each be measured during a single operating condition. A comparison of the first sensor response and the second sensor response during the single operating condition can aid in analyzing whether programming parameters are appropriate if the desired relationship between the first sensor response and the second sensor response is known. For example, where the first sensor response is pacing prevalence and the second sensor response is S1 amplitude, and both sensor responses are low relative to their respective individual thresholds, the system may recommend an adjustment of programming parameters.

Returning back to the embodiment depicted in FIG. 4, the system can generally be configured to propose an adjustment to the medical device parameters in the report 450. A user interface can be configured to display the proposed adjustment. In a variety of embodiments, the system has a user interface that is configured to display the association of the first sensor response to the first operating condition and the second sensor response to the second operating condition. In the example embodiment where the first and second sensor responses are pacing prevalence, the user interface can be configured to display the association of the first pacing prevalence to the first operating condition and the second pacing prevalence to the second operating condition.

Figure 5:
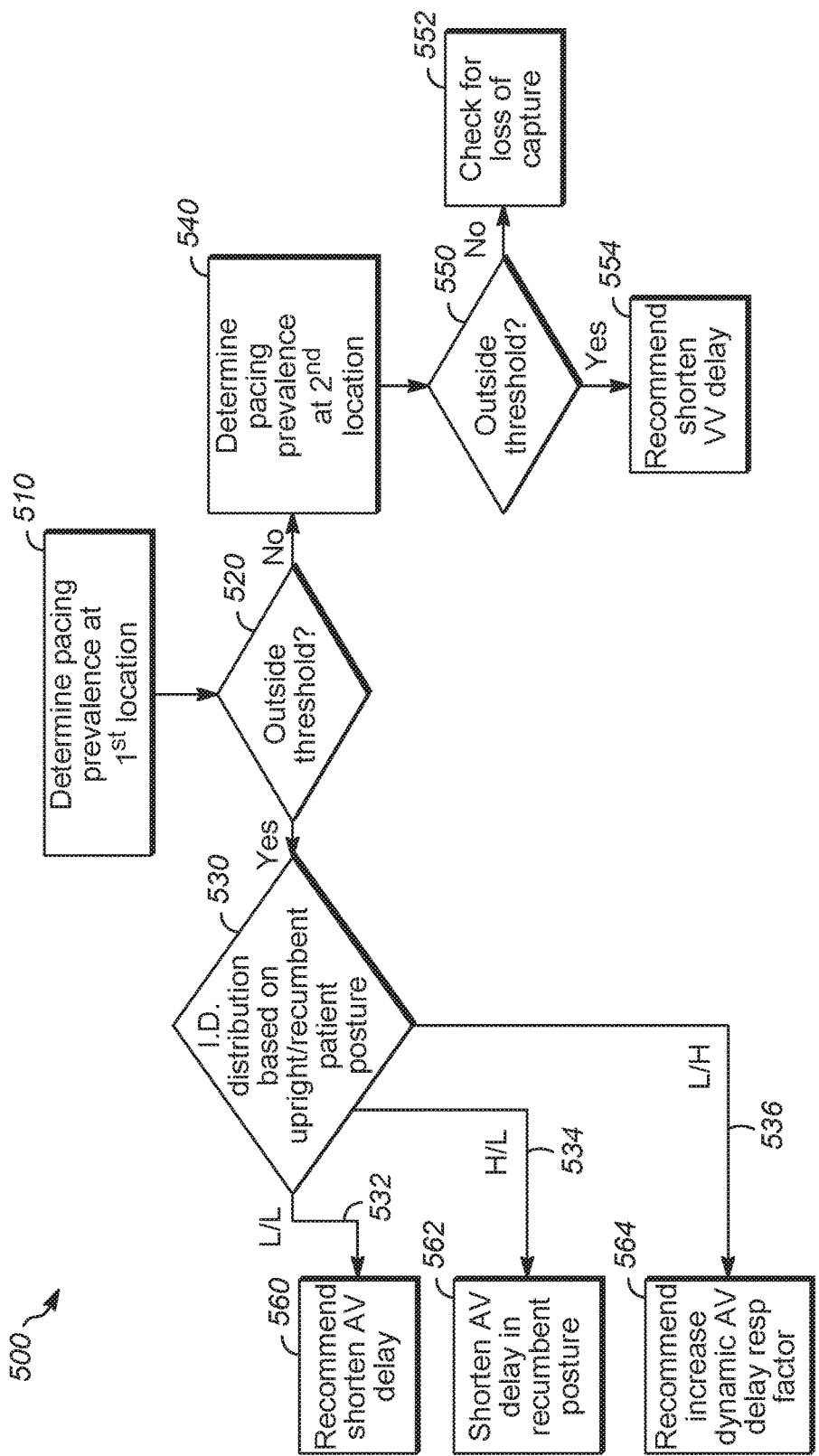
FIG. 5 depicts yet another flow chart consistent with one particular implementation of the technology disclosed herein.

FIG. 5 depicts a flow chart that is consistent with one particular implementation of the technology disclosed herein. This particular implementation is associated with a patient having a medical device providing cardiac resynchronization therapy (a CRT device). Analysis is conducted to determine a first performance metric, which is a first overall pacing prevalence at a first cardiac location 510 and whether the first overall pacing prevalence is outside of a threshold 520. In the current implementation the threshold corresponds to a minimum pacing percentage threshold that can be between 85%-99%, 90%-98%, or 95-97%. In one example the minimum pacing percentage threshold is 92%. In another example the minimum pacing percentage threshold is 95%. It is noted that other measurement values and thresholds can be used that are indicators of pacing percentage, such as sensed percentage.

In the current embodiment, the first cardiac location is the right ventricle. If the first overall pacing prevalence is outside of the threshold 520 or, more particularly, below the threshold minimum pacing percentage, the system identifies the distribution of the pacing prevalence during mutually exclusive operating conditions 530 which, in the current embodiment is upright/recumbent patient posture. As such, in this particular embodiment a first pacing prevalence is determined when the patient is in an upright posture, and a second pacing prevalence is determined when the patient is in a recumbent posture. In a similar embodiment, the mutually exclusive operating conditions can be time-of-day that divides up days by day time and nighttime or in multiple-hour intervals.

The first pacing prevalence and the second pacing prevalence are each compared to the threshold to determine whether they are outside of the threshold which, in this embodiment, means that the system determines whether the first pacing prevalence and the second pacing prevalence are below the threshold. If the first pacing prevalence and the second pacing prevalence are both below the threshold, meaning that pacing prevalence is low regardless of patient posture (L/L) 532, then the system recommends that the user shorten the A/V delay 560. If the first pacing prevalence (while upright) is high (and, therefore, not outside of the threshold), but the second pacing prevalence (while recumbent) is below the threshold (H/L) 534, then the system recommends that the user shorten the A/V delay when the patient is in a recumbent posture 562. In this respect, in some embodiments, the system is configured to dynamically adjust the A/V delay based on patient posture, such that the A/V delay is shortened when the patient is recumbent. In some embodiments, this feature needs to be turned on in order to dynamically adjust the A/V delay period.

Finally, if the first pacing prevalence (while upright) is outside of the threshold, but the second pacing prevalence (while recumbent) is within the threshold (L/H) 536, then the system recommends that the user increase the A/V delay response factor 564. In the scenario, the patient is being paced appropriately during the night time, but is being paced too infrequently during the day time. By increasing the A/V delay response factor, the device's reaction time is shortened so that it is more likely to pace the patient before an intrinsic beat occurs. In some embodiments, the device can be programed to automatically shorten the A/V delay response factor whenever the patient is exercising or reaches a minimum heart rate.

If the system determines that the first overall pacing prevalence at the first cardiac location is not outside of the threshold 520, then the system determines a second overall pacing prevalence at a second cardiac location 540 and determines whether the second overall pacing prevalence is outside of the threshold 550. In at least one embodiment the second cardiac location is the left ventricle. If the second overall pacing prevalence is not outside the threshold 550, then the system is configured to check for loss of capture 552 or, in the alternative, making a programming recommendation to a user to check for loss of capture, which will be described in more detail, below. If the second overall pacing prevalence is outside the threshold 550, then the system is configured to recommend shortening the interventricular delay 554. In some embodiments the system can be configured to recommend changes to other cardiac delay-related parameters, such as RA/LV delay or LA/LV delay.

Although not currently depicted, in some embodiments further analysis can be conducted by the system processing circuitry to determine a third pacing prevalence at the second cardiac location during the first operating condition and a fourth pacing prevalence at the second cardiac location during the second operating condition to provide further recommendations. While the embodiment depicted herein considers the overall pacing prevalence as the performance metric and particular pacing prevalence during the operating conditions as the sensor response, other performance metrics and sensor response data can also be considered, as described above.

In reference to loss of capture mentioned above in the discussion of FIG. 5, the processing circuitry of systems consistent with the technology disclosed herein are generally configured to either recommend or conduct a loss of capture analysis to determine whether the pacing voltage of the medical device is effective for treating the patient. If the system identifies a loss of capture, then it recommends an adjustment to programming parameters to increase the pacing voltage.

In identifying loss of capture, the system generally switches the cardiac medical device pacing status operating condition to OFF, operates the cardiac medical device with the pacing OFF and records the sensed S1 amplitude. System is configured to switch the pacing status of the cardiac medical device to ON, operate with the pacing ON, and record the paced S1 amplitude. The processing circuitry is configured to compare the paced amplitude to the sensed amplitude, and identify loss of capture if the sensed amplitude is larger than or substantially equal to the paced amplitude. Other approaches can also be used to identify loss of capture. For example, pre-ejection period (PEP) can be measured as some fiducial in QRS complex (q-point or R) to S1 as an indicator of tissue capture. Paced pre-ejection period is generally longer than intrinsic pre-ejection period largely due to two factors: (1) an R-event on a paced beat is close to the true initiation of electrical synchrony, whereas on an intrinsic beat R-event corresponds to the time point when the electrical activation reaches the RV-electrodes (in the apex) which happens after some time of initiation of electrical activation; and (2) a paced beat leads to electromechanical activation via slow cell-to-cell conduction whereas an intrinsic beat evokes the faster conduction pathways of the heart leading to a quicker overall ventricular activation. Note that if pre-ejection period is referenced from Q-point (rather than R-event) just the second factor is a contributor as the first factor is a non-issue.

Similarly, the end of ejection is delayed within the cardiac cycle in a paced beat as compared to an intrinsic beat due to slower cell-to-cell conduction, which results in a slower repolarization wave. As a result, total systolic interval is longer in a paced beat than an intrinsic beat. On the other hand, diastolic interval is shorter in a paced beat than a sensed beat (at comparable heart rates).

Loss of capture can be identified by switching the device pacing status to OFF, measuring and recording at least one of the time intervals described above, and comparing that with the corresponding time intervals recorded with the pacing status switched to ON. If the time intervals with pacing status ON are substantially different than those with pacing status OFF (longer for PEP and systolic interval, shorter for diastolic interval), we conclude that the tissue is captured. On the other hand, if the timing intervals with pacing status ON and OFF are similar, we conclude that the tissue is not captured.

Note, that the timing interval comparisons described above assume similar heart rates. Heart rates are known to impact timing intervals and thus may confound comparisons if changed substantially across comparisons (See, for example, A M Weissler, W S Harris & C D Schoenfeld, *Systolic Time Intervals in Heart Failure in Man*, Circulation 37(2), pp. 149-159 (February 1968)). If there are substantial changes in heart rate, corrections can be incorporated to yield HR independent systolic time indices that could be compared across pacing status ON and OFF conditions. One way of correcting timing intervals for heart rate is based on linear regression (See, for example, R P Lewis, S E Rittogers, W F Froester & H Boudoulas, *A Critical Review of the Systolic Time Intervals*, Circulation 56(2), pp. 146-158; (August 1977)).

Figure 6:
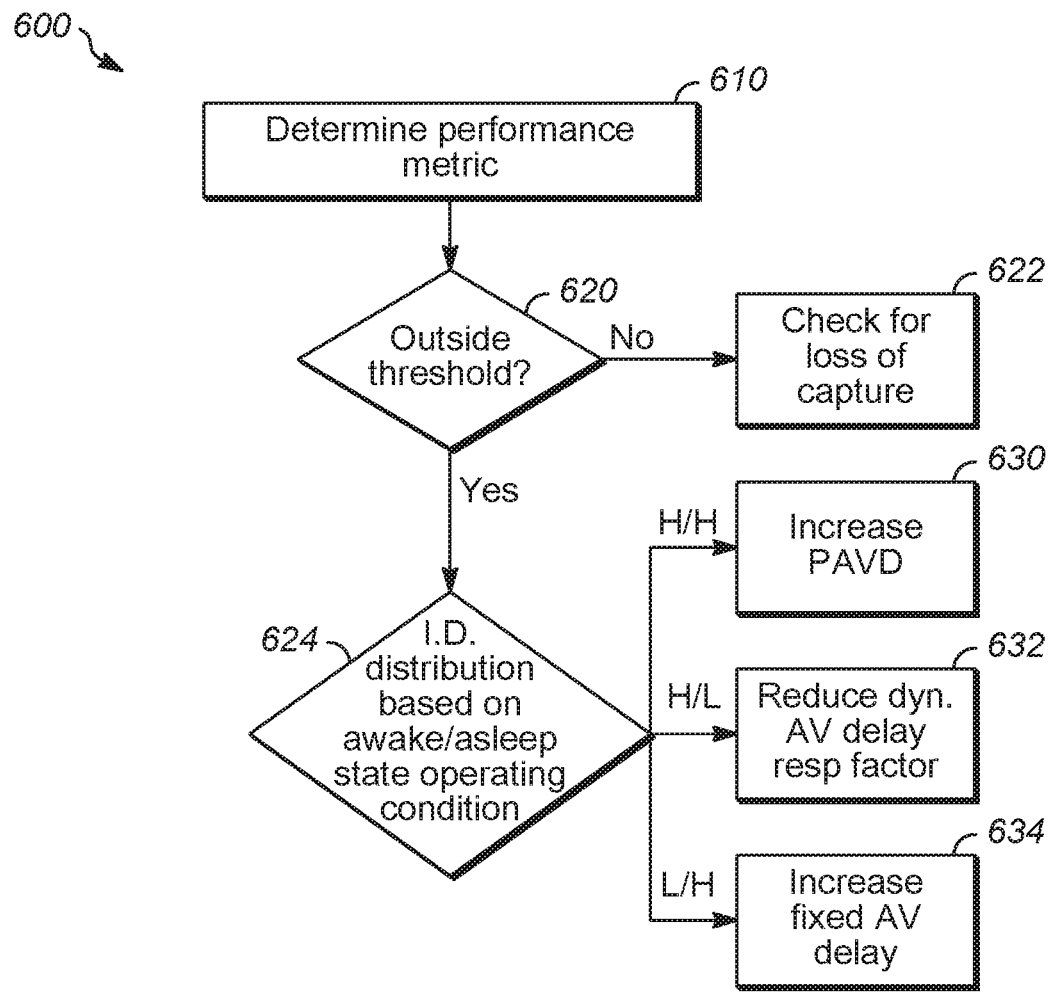
FIG. 6 depicts another flow chart consistent with a second particular implementation of the technology disclosed herein.

FIG. 6 depicts another particular implementation of the technology disclosed herein. This implementation 600 is associated with a patient having a medical device providing cardiac defibrillation, for example, where better outcomes are associated with lower pacing prevalence. Similar to the previous embodiment, analysis is conducted to determine a performance metric 610 and determine whether it is outside of a threshold 620. In the current embodiment the performance metric is an overall pacing prevalence at a particular cardiac location. Because lower pacing prevalence in this example scenario will generally correspond to better outcomes for a patient, the threshold corresponds to a maximum pacing percentage threshold that can be between 5% and 50%, 10% and 30%, or 15% and 20%, as examples. In one example the maximum pacing percentage threshold is 5%. In another example the maximum pacing percentage threshold is 10%. Other measurement values and thresholds can be used that are indicators of pacing percentage, such as sensed percentage.

In the current embodiment, the first cardiac location is the right ventricle. If the first overall pacing prevalence is outside of the threshold 620 or, more particularly, above the threshold minimum pacing percentage, the system identifies the distribution of the pacing prevalence during mutually exclusive operating conditions 624 which, in the current embodiment is patient awake/sleep state. As such, in this particular embodiment a first pacing prevalence is determined when the patient is awake, and a second pacing prevalence is determined when the patient is asleep. As described above, the patient awake/sleep state can be indicated through detecting operating conditions such as upright/recumbent patient posture, day time/nighttime, patient exertion level and patient metabolic state data.

The first pacing prevalence and the second pacing prevalence are each compared to the threshold to determine whether they are outside of the threshold 624 which, in this embodiment, means that the system determines whether the first pacing prevalence (while awake) and the second pacing prevalence (while asleep) are above the threshold. If the first pacing prevalence and the second pacing prevalence are both above the threshold, meaning that pacing prevalence is high regardless of patient sleep state (H/H) 630, then the system recommends that the clinical user increase the paced A/V delay 630. If the first pacing prevalence (while awake) is high (and, therefore, outside of the threshold), but the second pacing prevalence (while asleep) is below the threshold (H/L), then the system recommends that the user reduce the dynamic A/V delay response factor 632. Finally, if the first pacing prevalence (while awake) is outside of the threshold, but the second pacing prevalence (while asleep) is within the threshold (L/H), then the system recommends that the user increase the fixed A/V delay 634.

Similar to the embodiment described in FIG. 5, the system can be configured to check for loss of capture or recommend the user initiate a check for loss of capture 622 if the overall performance metric is not outside of the threshold 620. In some embodiments related to those depicted in FIGS. 5 and 6, the system is configured to evaluate loss of capture regardless of whether the performance metric is outside of the threshold. In such implementations the system can also be configured to display the results of the loss of capture analysis for consideration by the user.

Figure 7:
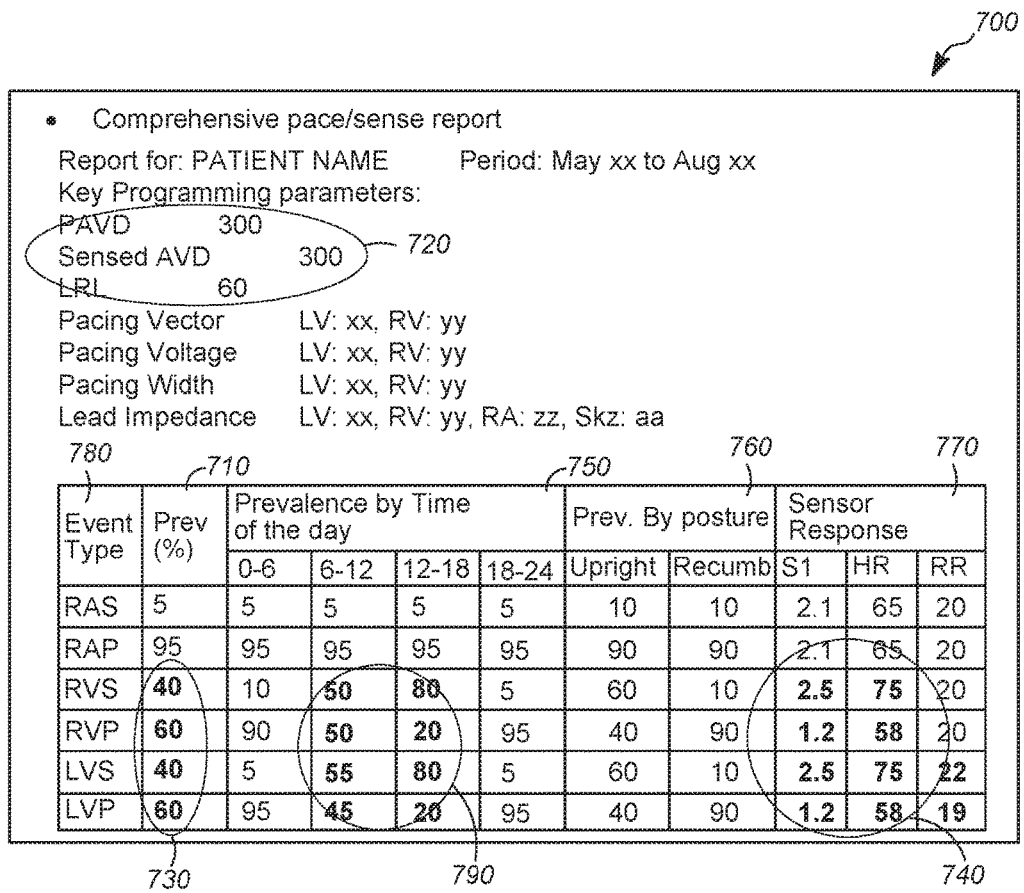
FIGS. 7-11 depicts first example screenshots of an interface of a programming device consistent with the technology disclosed herein.

FIG. 7 depicts an example screenshot of an interface of a programming device consistent with one example implementation of the technology disclosed herein. In the current example, the system is associated with a patient having a medical device providing CRT. A comprehensive pace/sense report 700 is generated by a system disclosed herein to interpret and communicate data to a clinical user. Key programming parameters 720 are displayed, which communicate the key medical device parameters in proximity to allow comparison by the user. An overall performance metric, which is overall pacing prevalence 710, is displayed for a number of cardiac locations 780 of the patient. Measured sensor response of each cardiac location is reported based on time-of-day 750 and posture 760 operating conditions, where the measured sensor response is pacing prevalence. It is noted that, in embodiments consistent with FIG. 7, the system is configured to identify more than two operating conditions associated with time-of-day. In this embodiment, four six-hour time ranges are possible for the time of day operating condition: 0-6, 6-12, 12-18 and 18-24.

Additional sensor responses 770 are reported for each of the cardiac locations, as well, which in this particular example are S1 amplitude, heart rate and respiration rate (RR). Data that may be an indicator of improper programming parameters are highlighted 730, 740, 790 as particularly relevant for the clinical user's review. The current display draws the user's attention to the fact that the right ventricular and left ventricular overall pacing prevalence is outside the desirable threshold by bolding the corresponding values 730. The display similarly draws attention to the pacing prevalence values that are outside of the threshold during particular operating conditions, specifically from 6:00 a.m. to 6:00 p.m. and when the patient is in an upright position. Other sensor responses 770 that are also unbalanced or otherwise undesirable are further highlighted 740 to draw attention to them.

In a variety of embodiments the clinical user can configure some particular parameters that are displayed on the comprehensive pace/sense report 700. While in the current embodiment the report 700 does not provide recommendations for programming adjustments, in at least some embodiments, programming adjustments are recommended by the system. FIGS. 8-11 depict example implementations where the system generates a programming recommendation and displays the recommendations to the system user.

Figure 8:
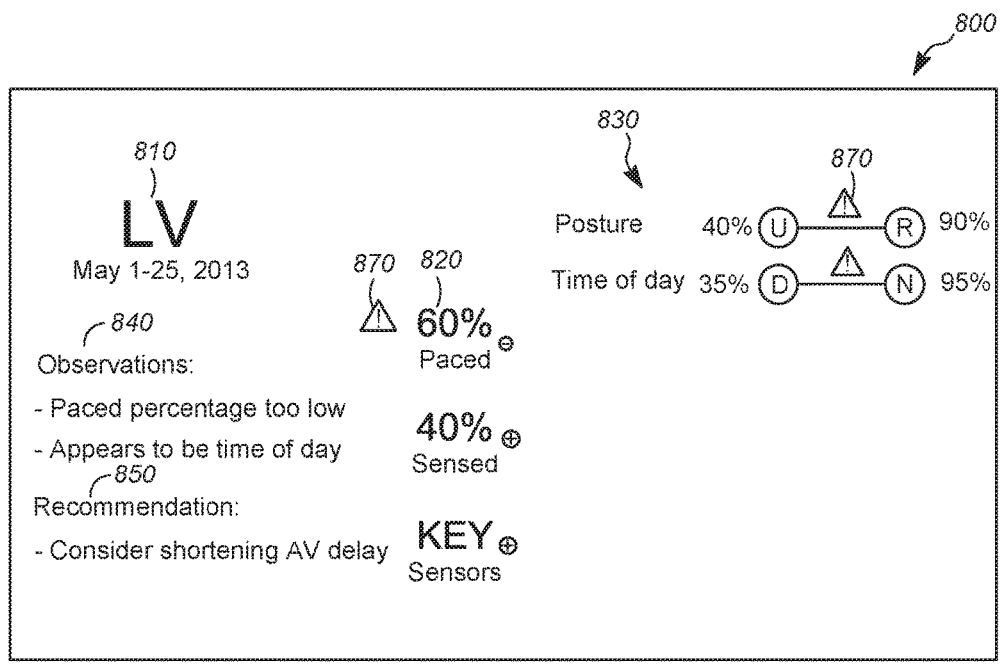
Figure 9:
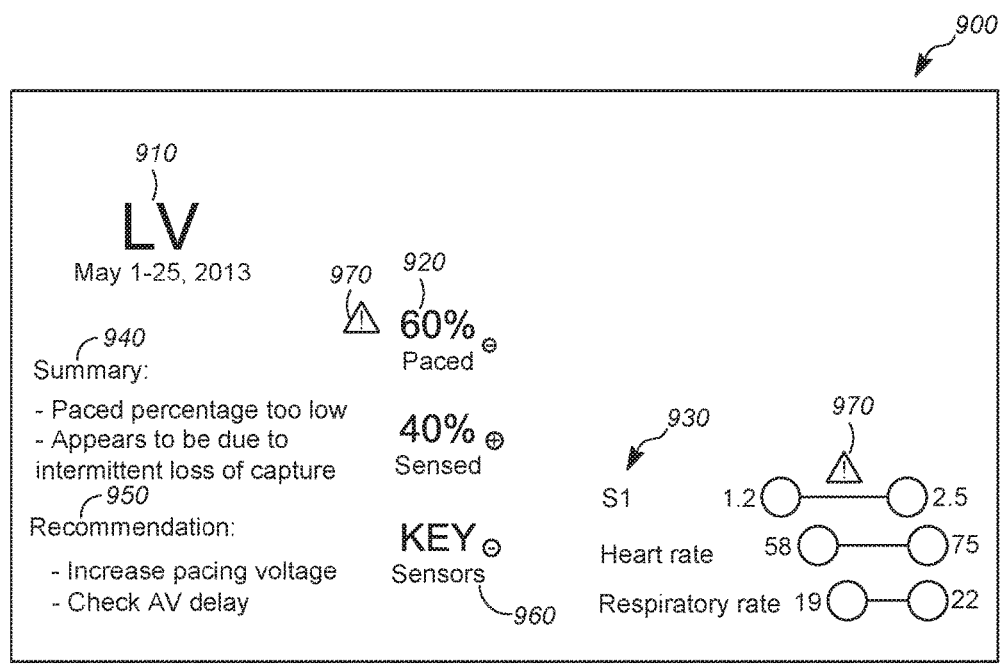

FIGS. 8 and 9 depict example interfaces of a programming device consistent with an example implementation where a medical device is providing a patient with cardiac rhythm therapy. With regard to FIG. 8, the display 800 shows a particular cardiac location that is being reported on, which is the left ventricle 810. The system displays an overall performance metric such as pacing prevalence 820, which can be expanded by the user so the interface displays data collected during each of the particular operating conditions 830. Caution symbols 870 are placed adjacent to particular data that demonstrates inadequate programming parameters. The system displays observations 840 and recommendations 850 based on the analysis described herein. The observations 840 on display 800 are, "Paced percentage too low" and "Appears to be time of day". The recommendation 850 is, "Consider shortening AV delay."

In FIG. 9 the display 900 shows a particular cardiac location that is being reported on, which is the left ventricle 910. The system displays an overall performance metric such as pacing prevalence 920. A graphic referring to the key sensor readings 960 can be selected by a user to display the particular key sensor readings 930. Caution symbols 970 are placed adjacent to particular data that demonstrates inadequate programming parameters. The system displays observations 940 and recommendations 950 based on the analysis described herein. The summary or observations 940 on display 900 are, "Paced percentage too low" and "Appears to be due to intermittent loss of capture". The recommendations 950 are, "Increase pacing voltage" and "Check AV delay."

Figure 10:
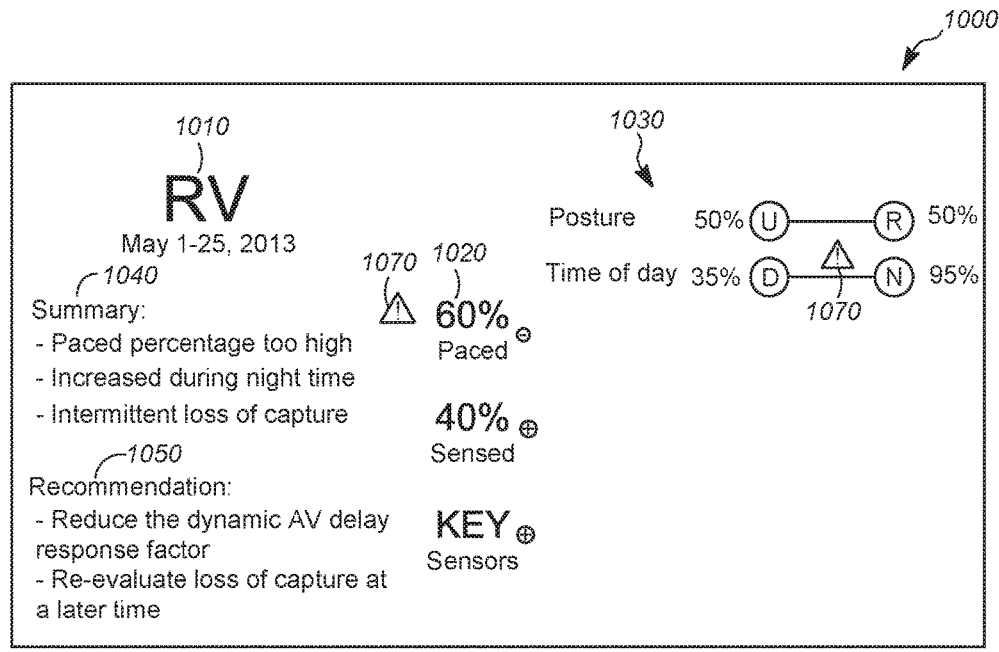
Figure 11:
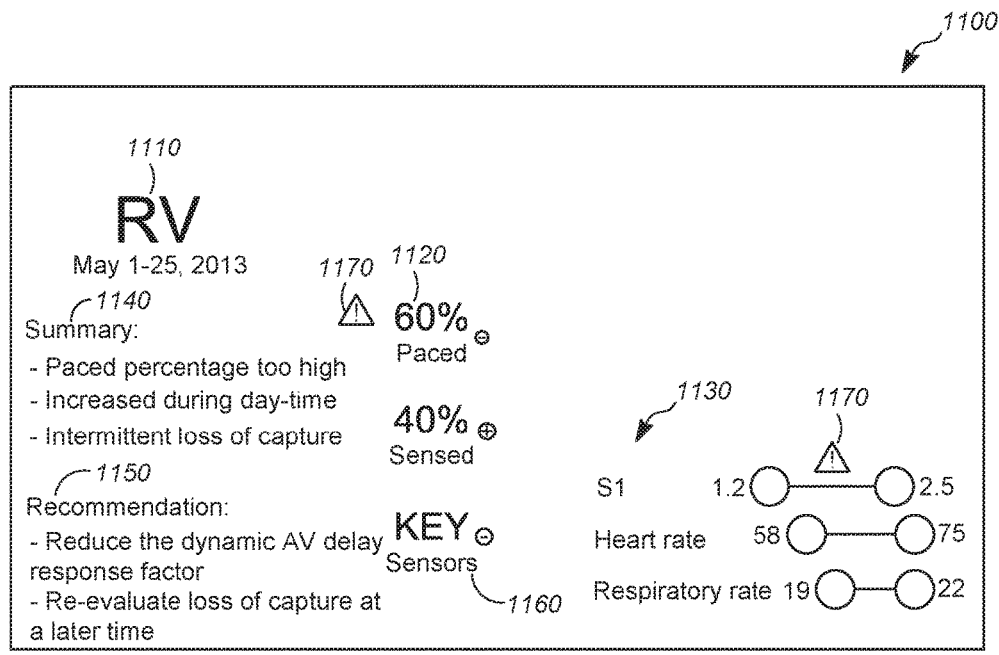

FIGS. 10 and 11 depict example interfaces of a programming device consistent with an example implementation where a medical device is an ICD, for example. With regard to FIG. 10, the display 1000 shows a particular cardiac location that is being reported on, which is the right ventricle 1010. The system displays an overall performance metric such as pacing prevalence 1020, which can be expanded by the user so the interface displays data collected during each of the particular operating conditions 1030, such as posture (upright and recumbent) and time of day (day time and night time). Caution symbols 1070 are placed adjacently to draw attention to particular data that demonstrates inadequate programming parameters. The system displays observations 1040 and recommendations 1050 based on the analysis described herein. The observations 1040 on display 1000 are, "Paced percentage too high" and "Increased during night time" and "Intermittent loss of capture". The recommendations 1050 are, "Reduce the dynamic AV delay response factor" and "Re-evaluate loss of capture at a later time."

In FIG. 11 the display 1100 similarly shows a particular cardiac location that is being reported on, which is the right ventricle 1110. The system displays an overall performance metric such as pacing prevalence 1120. A graphic referring to the key sensor readings 1160 can be selected by a user to display the particular data of the key sensor readings 1130. Caution symbols 1170 are placed adjacently to particular data that demonstrates inadequate programming parameters. The system displays observations 1140 and recommendations 1150 based on the analysis described herein. The observations 1140 on display 1100 are, "Paced percentage too high" and "Increased during day time" and "Intermittent loss of capture". The recommendations 1150 are, "Reduce the dynamic AV delay response factor" and "Re-evaluate loss of capture at a later time."

Programmer Hardware

Figure 12:
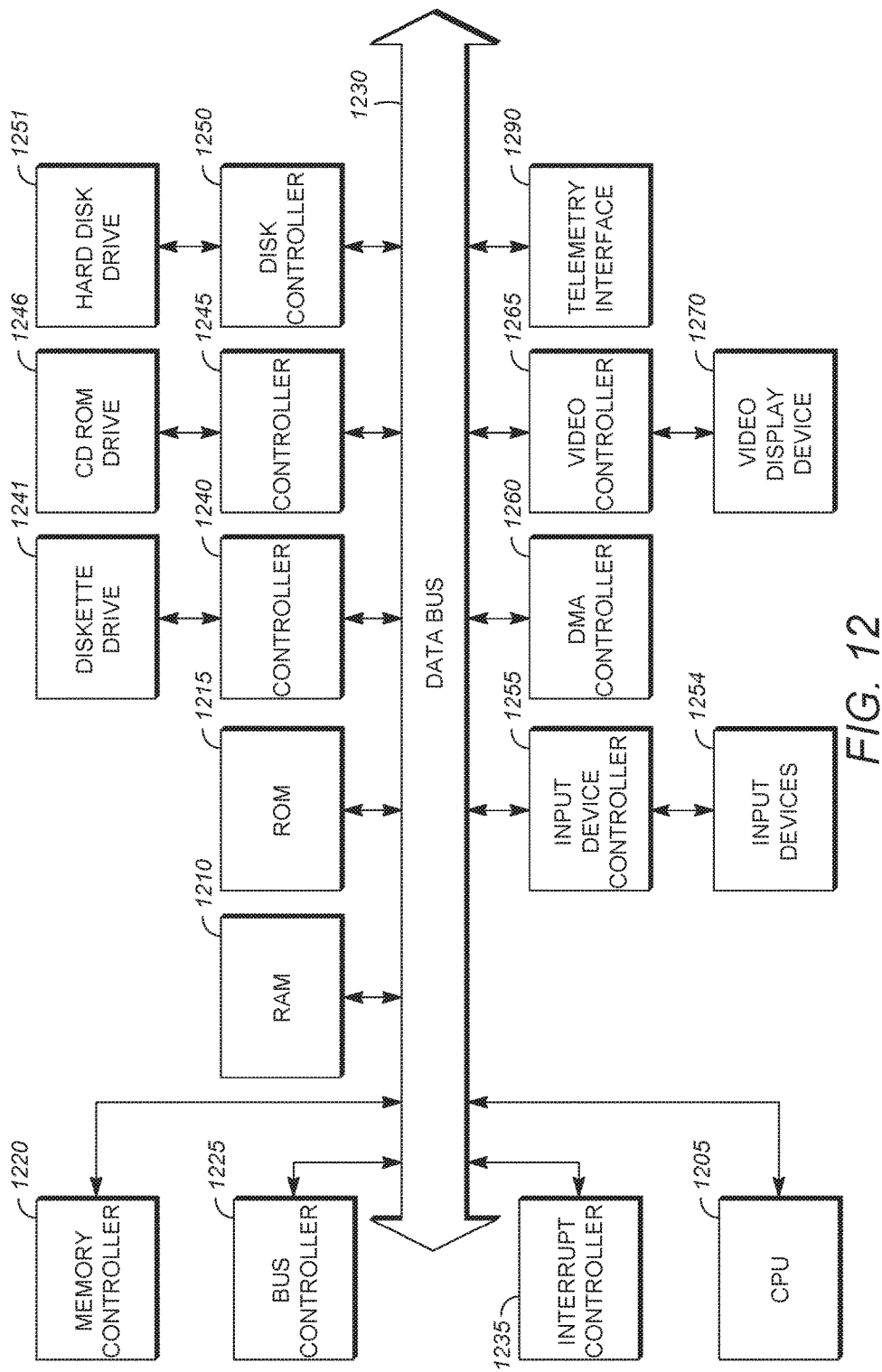
FIG. 12 is a schematic diagram of an implementation of the components of a programming device or user interface, in accordance with various embodiments.

Programming devices consistent with the technology disclosed herein can include components common to many computing devices. Referring now to FIG. 12, a diagram of various components is shown in accordance with some embodiments. However, it is not required that a programming device have all of the components illustrated in FIG. 12, and in some embodiments components depicted herein can be distributed among multiple devices.

In one embodiment, the programming device includes a central processing unit (CPU) 1205 or processor having processing circuitry, which may include a conventional microprocessor, random access memory (RAM) 1210 for temporary storage of information, and read-only memory (ROM) 1215 for permanent storage of information. A memory controller 1220 is provided for controlling system RAM 1210. A bus controller 1225 is provided for controlling data bus 1230, and an interrupt controller 1235 is used for receiving and processing various interrupt signals from the other system components.

Mass storage can be provided by diskette drive 1241, which is connected to bus 1230 by controller 1240, CD-ROM drive 1246, which is connected to bus 1230 by controller 1245, and hard disk drive 1251, which is connected to bus 1230 by controller 1250. User input to the programmer system may be provided by a number of input devices 1234. For example, a keyboard, touch screen, mouse, or more than one of these, can connected to bus 1230 by input device controller 1255. DMA controller 1260 is provided for performing direct memory access to system RAM 1210. A visual display is generated by a video controller 1265 or video output, which controls video display 1270. The external system can also include a telemetry interface 1290 or telemetry circuit which allows the external system to interface and exchange data with an implantable medical device. It will be appreciated that some embodiments may lack various elements illustrated in FIG. 12.

Implantable Device Hardware

Figure 13:
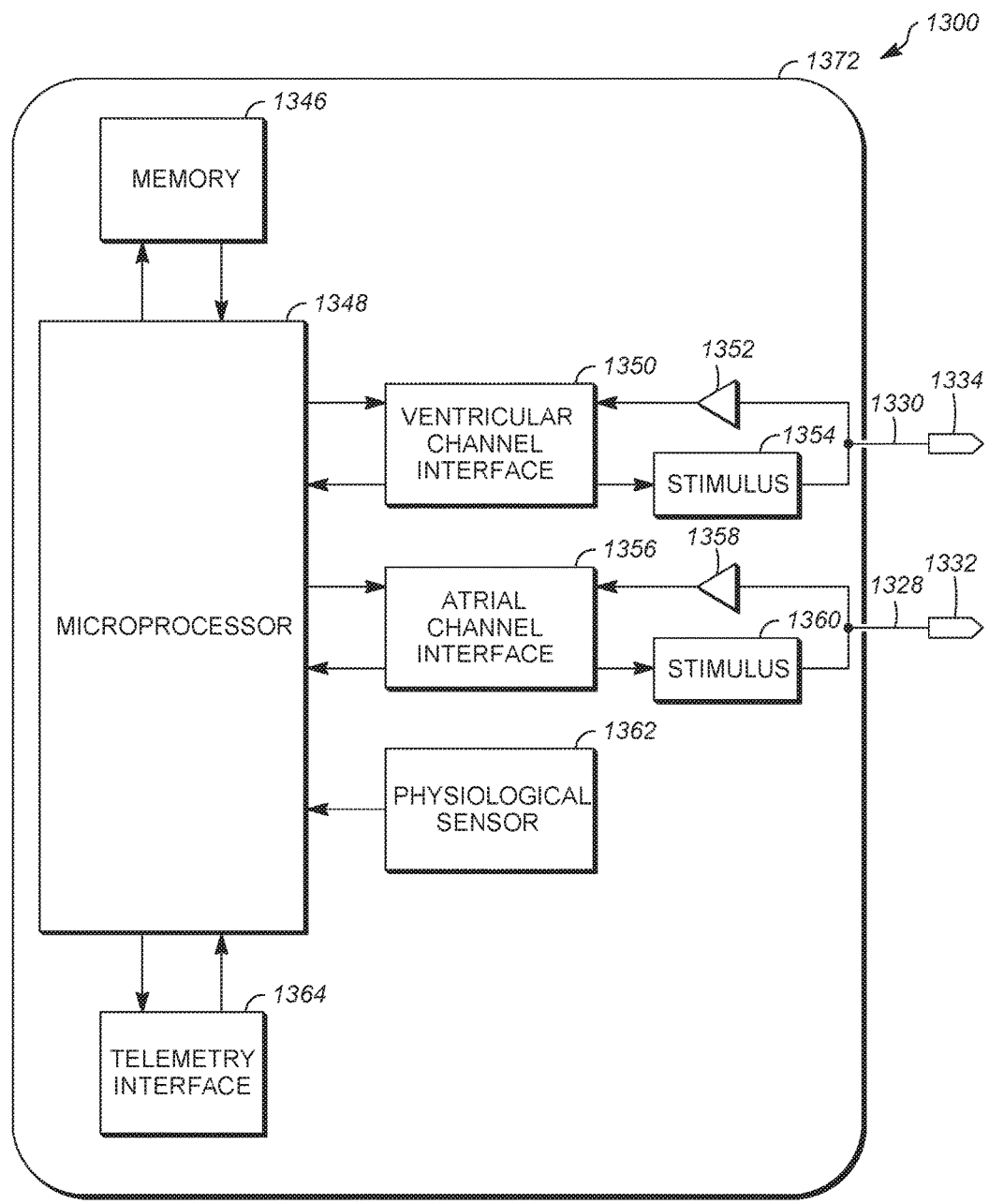
FIG. 13 is a schematic view of components of an implantable medical system in accordance with an embodiment.

Referring now to FIG. 13, some components of an exemplary implantable system 1300, such as an implantable CRM device, are schematically illustrated. The implantable medical system 1300 can include an implantable medical device 1372 coupled to one or more stimulation leads 1330 and 1328. The implantable device 1372 can also include one or more other physiological sensors 1362 such as an activity sensor, a posture sensor, or the like.

The implantable device 1372 can include a microprocessor 1348 (or processor) having processing circuitry that communicates with a memory 1346 via a bidirectional data bus. The memory 1346 typically comprises ROM or RAM for program storage and RAM for data storage. The implantable device can be configured to execute various operations such as processing of signals and execution of methods as described herein. A telemetry interface 1364 is also provided for communicating with an external unit, such as a programmer device or a patient management system.

The implantable device can include ventricular sensing and pacing channels comprising sensing amplifier 1352, output circuit 1354, and a ventricular channel interface 1350 which communicates bidirectionally with a port of the microprocessor 1348. The ventricular sensing and pacing channel can be in communication with stimulation lead 1330 and electrode 1334. The implantable device can include atrial sensing and pacing channels comprising sensing amplifier 1358, output circuit 1360, and an atrial channel interface 1356 which communicates bidirectionally with a port of microprocessor 1348. The atrial sensing and pacing channel can be in communication with stimulation lead 1328 and electrode 1332. For each channel, the same lead and electrode can be used for both sensing and pacing. The channel interfaces 1350 and 1356 can include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as "arranged", "arranged and configured", "constructed and arranged", "constructed", "manufactured and arranged", and the like.

One of ordinary skill in the art will understand that the modules, circuitry, and methods shown and described herein with regard to various embodiments can be implemented using software, hardware, and combinations of software and hardware. As such, the illustrated and/or described modules and circuitry are intended to encompass software implementations, hardware implementations, and software and hardware implementations.

All publications and patent applications in this specification are indicative of the level of ordinary skill in the art to which this technology pertains. All publications and patent applications are herein incorporated by reference to the same extent as if each individual publication or patent application was specifically and individually indicated by reference.

This application is intended to cover adaptations or variations of the present subject matter. It is to be understood that the above description is intended to be illustrative, and not restrictive.

We claim:

1. A system comprising:
   a cardiac medical device configured to be implanted in a patient, the medical device comprising sensing circuitry configured to sense sufficient data to determine a first overall performance metric of the cardiac medical device at a first cardiac location of a patient, wherein the overall performance metric characterizes the medical device performance over a first operating condition and a second operating condition, where the first and second operating conditions are mutually exclusive;
   processing circuitry in communication with the sensing circuitry configured to identify a first performance metric during the first operating condition, a second performance metric during the second operating condition, and the first overall performance metric; and
   a user interface configured to display an association of the first performance metric with the first operating condition and the second performance metric to the second operating condition.

2. The system of claim 1, further comprising an accelerometer configured to determine patient posture, wherein the accelerometer is in communication with the processing circuitry and the first operating condition is recumbent patient posture and the second operating condition is upright patient posture.

3. The system of claim 1, wherein the performance metric is pacing prevalence.

4. The system of claim 1 wherein the first operating condition is nighttime and the second operating condition is day time.

5. The system of claim 1, further comprising a user interface, wherein the system is configured to display a programming recommendation on the user interface based on the first performance metric, the second performance metric, the first operating condition, and the second operating condition.

6. The system of claim 5, wherein the programming recommendation is to evaluate loss of capture.

7. The system of claim 1, wherein the sensing circuitry is further configured to determine a second overall performance metric at a second cardiac location of a patient; and the processing circuitry is further configured to associate a third performance metric with the first operating condition and a fourth performance metric with the second operating condition.

* * * * *